(12) United States Patent
Hoyle et al.

(10) Patent No.: US 10,357,149 B2
(45) Date of Patent: Jul. 23, 2019

(54) MEDICAL IMAGING DEVICE USING THERMALLY CONDUCTING LENS CRADLE

(71) Applicant: INTEGRATED ENDOSCOPY, INC., Rancho Santa Margarita, CA (US)

(72) Inventors: Lonnie R. Hoyle, Mission Viejo, CA (US); Kais Almarzouk, Tustin, CA (US)

(73) Assignee: INTEGRATED ENDOSCOPY, INC., Rancho Santa Margarita, CA (US)

( * ) Notice: Subject to any disclaimer, the term of this patent is extended or adjusted under 35 U.S.C. 154(b) by 567 days.

(21) Appl. No.: 14/567,879

(22) Filed: Dec. 11, 2014

(65) Prior Publication Data

US 2015/0164312 A1    Jun. 18, 2015

Related U.S. Application Data

(60) Provisional application No. 61/916,043, filed on Dec. 13, 2013.

(51) Int. Cl.
*A61B 1/07* (2006.01)
*A61B 1/12* (2006.01)
(Continued)

(52) U.S. Cl.
CPC .......... *A61B 1/128* (2013.01); *A61B 1/00096* (2013.01); *A61B 1/00114* (2013.01);
(Continued)

(58) Field of Classification Search
CPC .............. A61B 1/0008; A61B 1/00096; A61B 1/00163; A61B 1/00165; A61B 1/00174;
(Continued)

(56) References Cited

U.S. PATENT DOCUMENTS

| 1,632,290 A | 6/1927 | Heymer |
| 4,148,550 A | 4/1979 | MacAnally |

(Continued)

FOREIGN PATENT DOCUMENTS

| JP | 11-47080 | 2/1999 |
| JP | 2002-148520 | 5/2002 |

(Continued)

OTHER PUBLICATIONS

International Search Report and Written Opinion dated Apr. 13, 2015 in International Application No. PCT/US2014/069842.

(Continued)

*Primary Examiner* — Ryan N Henderson
*Assistant Examiner* — Pamela F Wu
(74) *Attorney, Agent, or Firm* — Knobbe, Martens, Olson & Bear LLP (57) ABSTRACT

Various embodiments comprise endoscopes (e.g., arthroscopes) for viewing inside a cavity of a body. The endoscopes may include at least one solid state emitter such as a light emitting diode (LED) located at the distal end of the endoscope. The endoscope may comprise a thermally conductive cradle attached to the distal end of the endoscope. The thermally conductive cradle may be configured to dissipate heat generated by the solid state emitter away from the distal end of the endoscope. The thermally conductive cradle may also be electrically conductive. Further, the thermally conductive cradle may also function as a support structure for a plurality of lenses.

29 Claims, 4 Drawing Sheets

(51) Int. Cl.
*A61B 1/06* (2006.01)
*A61B 1/317* (2006.01)
*A61B 1/055* (2006.01)
*A61B 1/00* (2006.01)

(52) U.S. Cl.
CPC ............ *A61B 1/055* (2013.01); *A61B 1/0676* (2013.01); *A61B 1/0684* (2013.01); *A61B 1/317* (2013.01)

(58) Field of Classification Search
CPC ............ A61B 1/00177; A61B 1/00179; A61B 1/00181; A61B 1/00183; A61B 1/00188; A61B 1/0019; A61B 1/00193; A61B 1/002; A61B 1/04; A61B 1/042; A61B 1/05; A61B 1/051; A61B 1/053; A61B 1/055; A61B 1/06; A61B 1/0607; A61B 1/0615; A61B 1/0623; A61B 1/063; A61B 1/0661; A61B 1/0669; A61B 1/0676; A61B 1/0684; A61B 1/128
USPC .................. 600/109–112, 127–130, 160–182
See application file for complete search history.

(56) References Cited

U.S. PATENT DOCUMENTS

| | | | |
|---|---|---|---|
| 4,730,909 A | 3/1988 | Takahashi | |
| 4,784,118 A | 11/1988 | Fantone | |
| 4,850,342 A | 7/1989 | Hashiguchi et al. | |
| 5,020,893 A | 6/1991 | Karst et al. | |
| 5,142,410 A | 8/1992 | Ono et al. | |
| 5,601,525 A | 2/1997 | Okada | |
| 5,647,840 A * | 7/1997 | D'Amelio | A61B 1/00091 600/169 |
| 5,666,222 A | 9/1997 | Ning | |
| 5,700,236 A | 12/1997 | Sauer et al. | |
| 5,865,725 A | 2/1999 | Arai et al. | |
| 5,980,453 A | 11/1999 | Forkey et al. | |
| 5,999,344 A | 12/1999 | Wulfsberg et al. | |
| 6,248,060 B1 | 6/2001 | Buess et al. | |
| 6,364,830 B1 | 4/2002 | Durell | |
| 6,398,723 B1 | 6/2002 | Kehr et al. | |
| 6,424,473 B1 | 7/2002 | Nakane et al. | |
| 6,471,640 B1 | 10/2002 | Frische et al. | |
| 6,635,010 B1 | 10/2003 | Lederer | |
| 6,638,216 B1 | 10/2003 | Durell | |
| 6,692,431 B2 | 2/2004 | Kazakevich | |
| 6,701,181 B2 | 3/2004 | Tang et al. | |
| 6,818,818 B2 | 11/2004 | Bareis | |
| 6,855,109 B2 | 2/2005 | Obata et al. | |
| 6,921,920 B2 | 7/2005 | Kazakevich | |
| 6,962,565 B2 | 11/2005 | Nakamura | |
| 7,063,663 B2 | 6/2006 | Kazakevich | |
| 7,345,312 B2 | 3/2008 | Kazakevich | |
| 7,413,543 B2 | 8/2008 | Banik et al. | |
| 7,540,645 B2 | 6/2009 | Kazakevich | |
| 7,683,926 B2 | 3/2010 | Schechterman et al. | |
| 7,896,804 B2 | 3/2011 | Uchimura | |
| 7,959,338 B2 | 6/2011 | Kazakevich | |
| 7,976,462 B2 | 7/2011 | Wright et al. | |
| 8,636,652 B2 | 1/2014 | Wright et al. | |
| 8,959,338 B2 | 2/2015 | Snow et al. | |
| 2002/0103420 A1 | 8/2002 | Coleman et al. | |
| 2002/0154215 A1 | 10/2002 | Schechterman et al. | |
| 2002/0183623 A1 | 12/2002 | Tang et al. | |
| 2003/0018238 A1 | 1/2003 | Obata et al. | |
| 2003/0042493 A1 | 3/2003 | Kazakevich | |
| 2003/0050534 A1 | 3/2003 | Kazakevich | |
| 2003/0120129 A1 | 6/2003 | Nakamura | |
| 2004/0031517 A1 | 2/2004 | Bareis | |
| 2004/0092794 A1 | 5/2004 | Chin et al. | |
| 2005/0075538 A1 | 4/2005 | Banik et al. | |
| 2006/0041193 A1* | 2/2006 | Wright | A61B 1/00096 600/179 |
| 2006/0258902 A1 | 11/2006 | Spivey et al. | |
| 2006/0293565 A1 | 12/2006 | Uchimura | |
| 2007/0173695 A1* | 7/2007 | Hirata | A61B 1/00096 600/152 |
| 2008/0062540 A1 | 3/2008 | Scholer | |
| 2008/0130311 A1 | 6/2008 | Kazakevich | |
| 2009/0018397 A1 | 1/2009 | Scholly et al. | |
| 2009/0219713 A1 | 9/2009 | Siemiet et al. | |
| 2011/0092772 A1* | 4/2011 | Weber | A61B 1/0008 600/178 |
| 2011/0263941 A1 | 10/2011 | Wright et al. | |
| 2012/0029289 A1 | 2/2012 | Kucklick | |
| 2012/0176669 A1 | 7/2012 | Kiedrowski | |
| 2013/0345507 A1 | 12/2013 | Wright et al. | |

FOREIGN PATENT DOCUMENTS

| | | |
|---|---|---|
| JP | 2002-224015 | 8/2002 |
| JP | 2003-021792 | 1/2003 |
| JP | 2003-024276 | 1/2003 |
| WO | WO 98/35607 | 8/1998 |
| WO | WO 03/022135 | 3/2003 |
| WO | WO 03/022435 | 3/2003 |
| WO | WO 2004/036266 | 4/2004 |

OTHER PUBLICATIONS

Office Action dated Nov. 6, 2018, in Japanese application No. 2016-558537.
Restriction Requirement issued in U.S. Appl. No. 13/786,220 dated Dec. 24, 2013, in 8 pages.
Response to Restriction Requirement filed in U.S. Appl. No. 13/786,220 dated Apr. 24, 2014, in 2 pages.
Non-Final Office Action issued in U.S. Appl. No. 13/786,220 dated Jun. 25, 2014, in 12 pages.
Amendment filed in U.S. Appl. No. 13/786,220 dated Dec. 19, 2014, in 10 pages.
Final Office Action issued in U.S. Appl. No. 13/786,220 dated Mar. 26, 2015, in 15 pages.
Amendment filed in U.S. Appl. No. 13/786,220 dated Jul. 27, 2015, in 7 pages.
Non-Final Office Action issued in U.S. Appl. No. 13/786,220 dated Nov. 27, 2015, in 11 pages.
Amendment filed in U.S. Appl. No. 13/786,220 dated May 25, 2016, in 8 pages.
Final Office Action issued in U.S. Appl. No. 13/786,220 dated Sep. 7, 2016, in 11 pages.
Amendment filed in U.S. Appl. No. 13/786,220 dated Mar. 6, 2017, in 8 pages.
Non-Final Office Action issued in U.S. Appl. No. 13/786,220 dated Jun. 22, 2017, in 10 pages.
Amendment filed in U.S. Appl. No. 13/786,220 dated Dec. 22, 2017, in 9 pages.
Final Office Action issued in U.S. Appl. No. 13/786,220 dated Jan. 25, 2018, in 13 pages.
Amendment filed in U.S. Appl. No. 13/786,220 dated Jul. 25, 2018, in 11 pages.

\* cited by examiner

MEDICAL IMAGING DEVICE USING THERMALLY CONDUCTING LENS CRADLE

CROSS-REFERENCE TO RELATED APPLICATION

This application claims the benefit of priority of U.S. Provisional Application No. 61/916,043 filed on Dec. 13, 2013, titled "Medical Imaging Device Using Thermally Conducting Lens Cradle," which is incorporated by reference herein in its entirety.

This application is also related to U.S. application Ser. No. 11/099,435 filed on Apr. 5, 2005, now U.S. Pat. No. 7,976,462, which is also incorporated by reference herein in its entirety.

BACKGROUND

Various embodiments herein relate generally to endoscopes, arthroscopes, and other medical imaging devices. Endoscopes can be inserted into the body to form images of features within a cavity therein. Endoscopes generally include an elongate tubular structure that includes optics for imaging. Endoscopes may additionally be configured to provide illumination. Since endoscopes can provide images of within the patient's body, endoscopes are useful diagnostic and/or surgical tools.

SUMMARY

The systems, methods and devices of this disclosure each have several innovative aspects, no single one of which is solely responsible for the desirable attributes disclosed herein.

Various innovative aspects of the subject matter described in this disclosure can be implemented in the following embodiments:

Embodiment 1: An endoscope, comprising:
a proximal end portion;
a distal end portion;
a plurality of lenses disposed in an optical path extending from said distal end portion to said proximal end portion such that an image of an object at the distal end portion can be formed at the proximal end portion;
at least one solid state emitter disposed at the distal end portion, the at least one solid state emitter generating heat when activated; and
a thermally conductive cradle forming an elongate inner open region configured to house said plurality of lenses, said thermally conductive cradle attached to the distal end portion, the thermally conductive cradle configured to dissipate heat generated by the at least one solid state emitter away from the distal end portion, wherein the thermally conductive cradle comprises copper.

Embodiment 2: The endoscope of Embodiment 1, wherein said endoscope comprises an arthroscope.

Embodiment 3: The endoscope of any of Embodiments 1-2, wherein the at least one solid state emitter comprises at least one light emitting diode.

Embodiment 4: The endoscope of any of Embodiments 1-3, wherein said plurality of lenses comprise rod lenses having lengths and widths, said lengths being longer than said widths.

Embodiment 5: The endoscope of any of Embodiments 1-4, wherein the thermally conductive cradle comprises separate first and second sections, wherein the first section and second section comprise portions of a right circular cylinder physically separated by a gap along a longitudinal length of the right circular cylinder.

Embodiment 6: The endoscope of Embodiment 5, wherein the first and second sections have substantially equal size.

Embodiment 7: The endoscope of any of Embodiments 5-6, wherein the first and second sections each comprise substantially a half of said right circular cylinder.

Embodiment 8: The endoscope of any of Embodiments 5-7, wherein the first half and the second half each has two longitudinal edges, and wherein a first longitudinal edge of the first half and a first longitudinal edge of the second half are separated by a space at least 0.5 millimeter.

Embodiment 9: The endoscope of any of Embodiments 5-8, wherein a second longitudinal edge of the first half and a second longitudinal edge of the second half are physically separated by a space.

Embodiment 10: The endoscope of any of Embodiments 5-9, wherein a second longitudinal edge of the first half and a second longitudinal edge of the second half are physically spaced apart by a spacer.

Embodiment 11: The endoscope of any of Embodiments 5-10, further comprising:
a first electrical line connected to a cathode of one of the at least one solid state emitters; and
a second electrical line connected to an anode of one of the at least one solid state emitter,
wherein the first and second electrical lines are disposed in the space between said first and second sections.

Embodiment 12: The endoscope of Embodiment 11, wherein the first and second electrical lines comprise electrical wires.

Embodiment 13: The endoscope of any of Embodiments 1-12, wherein the thermally conductive cradle is electrically conductive and said the thermally conductive cradle provides at least one electrical path to the at least one solid state emitter.

Embodiment 14: The endoscope of any of Embodiments 1-13, wherein the first section is electrically connected to a cathode on at least one of said at least one solid state emitter and the second section is electrically connected to an anode on at least one of said at least one solid state emitter.

Embodiment 15: The endoscope of any of Embodiments 1-14, further comprising an outer tube surrounding the thermally conductive cradle.

Embodiment 16: The endoscope of any of Embodiments 1-15, wherein said cradle is electrically insulated from said outer tube.

Embodiment 17: The endoscope of any of Embodiments 1-16, wherein the distal end comprises a passageway forming a portion of the optical path, wherein the passageway comprises first and second reflective surfaces, such that the portion of the optical path through the passageway does not include a glass optical element.

Embodiment 18: The endoscope of any of Embodiments 1-18, wherein the first and the second reflective surfaces comprise metallized substrates.

Embodiment 19: The endoscope of Embodiment 18, wherein the substrates include glass.

Embodiment 20: The endoscope of any of Embodiments 18-19, wherein inner surfaces of the substrates that are adjacent to the passageway are metallized.

Embodiment 21: The endoscope of any of Embodiments 1-20, wherein the at least one solid state emitter is disposed on a base.

Embodiment 22: The endoscope of Embodiment 21, wherein the base comprises a thermally conducting material.

Embodiment 23: The endoscope of any of Embodiments 21-22, wherein the base comprises a ceramic material.

Embodiment 24: The endoscope of any of Embodiments 21-23, wherein the base comprises electrically conducting pathways configured to provide electrical power to the at least one solid state emitter.

Embodiment 25: The endoscope of any of Embodiments 21-24, wherein at least a portion of the base is metallized.

Embodiment 26: An endoscope, comprising:
 a proximal end portion;
 a distal end portion;
 at least one solid state emitter disposed at the distal end portion, the at least one solid state emitter generating heat when activated;
 a cradle attached to the distal end portion, wherein the cradle is thermally conductive and configured to dissipate heat generated by the at least one solid state emitter away from the distal end portion, wherein the cradle is further electrically conductive and is configured to provide an electrical path to the at least one solid state emitter; and
 at least one lens disposed inside the cradle.

Embodiment 27: The endoscope of Embodiment 26, wherein the endoscope comprises an arthroscope.

Embodiment 28: The endoscope of any of Embodiments 26-27, wherein the at least one solid state emitter comprises at least one light emitting diode.

Embodiment 29: The endoscope of any of Embodiments 26-28, wherein the at least one lens comprises a rod lens having a length and a width, said length being longer than said width.

Embodiment 30: The endoscope of any of Embodiments 26-30, wherein the cradle comprises copper.

Embodiment 31: The endoscope of any of Embodiments 26-31, further comprising an outer tube surrounding the thermally conductive cradle.

Embodiment 32: The endoscope of Embodiment 31, wherein the cradle is electrically insulated from said outer tube.

Embodiment 33: The endoscope of any of Embodiments 26-32, wherein the distal end comprises a passageway forming a portion of the optical path, wherein the passageway comprises first and second reflective surfaces, such that the portion of the optical path through the passageway does not include a glass optical element.

Embodiment 34: The endoscope of Embodiment 33, wherein the first and the second reflective surfaces comprise metallized substrates.

Embodiment 35: The endoscope of any of Embodiments 33-34, wherein the substrates include glass.

Embodiment 36: The endoscope of any of Embodiments 33-35, wherein inner surfaces of the substrates that are adjacent to the passageway are metallized.

Embodiment 37: The endoscope of any of Embodiments 26-36, wherein the at least one solid state emitter is disposed on a base.

Embodiment 38: The endoscope of any Embodiment 37, wherein the base comprises a thermally conducting material.

Embodiment 39: The endoscope of any of Embodiments 37-38, wherein the base comprises a ceramic material.

Embodiment 40: The endoscope of any of Embodiments 37-39, wherein the base comprises electrically conducting pathways configured to provide electrical power to the at least one solid state emitter.

Embodiment 41: The endoscope of any of Embodiments 37-40, wherein at least a portion of the base is metallized.

Embodiment 42: A method of using an endoscope, the method comprising:
 causing at least one solid state emitter to generate heat, wherein the at least one solid state emitter is disposed on a distal end portion of the endoscope; and
 dissipating heat generated by the at least one solid state emitter away from the distal end portion via a thermally conductive cradle attached to the distal end portion,
 wherein the thermally conductive cradle comprises copper.

Embodiment 43: The method of Embodiment 42, wherein the thermally conductive cradle comprises separate first and second sections, wherein the first section and the second section comprise portions a right circular cylinder physically separated by a gap along a longitudinal length of the right circular cylinder.

Embodiment 44

The method of any of Embodiments 42-43, wherein the thermally conductive cradle is further electrically conductive, and wherein the method further comprises providing electricity to the at least one solid state emitter via the thermally conductive cradle.

Embodiment 45: The method of any of Embodiments 42-44, wherein the endoscope comprises at least one rod lens disposed inside the thermally conductive cradle.

Embodiment 46: An endoscope, comprising:
 a proximal end portion;
 a distal end portion;
 a plurality of lenses disposed in an optical path extending from said distal end portion to said proximal end portion such that an image of an object at the distal end portion can be formed at the proximal end portion;
 at least one solid state emitter disposed at the distal end portion, the at least one solid state emitter generating heat when activated; and
 a thermally conductive cradle comprising an elongate inner open region configured to house said plurality of lenses, said thermally conductive cradle attached to the distal end portion,
 wherein the thermally conductive cradle comprises separate first and second sections, wherein the first section and the second section comprise portions a right circular cylinder physically separated by a gap along a longitudinal length of the right circular cylinder.

Embodiment 47: The endoscope of Embodiment 46, wherein the first and second sections have substantially equal size.

Embodiment 48: The endoscope of any of Embodiments 46-47, wherein the first and second sections each comprise substantially a half of said right circular cylinder.

Embodiment 49: The endoscope of Embodiment 48, wherein the first half and the second half each has two longitudinal edges, and wherein a first longitudinal edge of the first half and a first longitudinal edge of the second half are separated by a space at least 0.5 millimeter.

Embodiment 50: The endoscope of Embodiment 49, wherein a second longitudinal edge of the first half and a second longitudinal edge of the second half are physically spaced apart by a spacer.

Embodiment 51: The endoscope of any of Embodiments 49-50, wherein a second longitudinal edge of the first half and a second longitudinal edge of the second half are physically separated by a space.

Embodiment 52: The endoscope of any of Embodiments 46-51, further comprising:

a first electrical line connected to a cathode of one of the at least one solid state emitters; and a second electrical line connected to an anode of one of the at least one solid state emitters, wherein the first and second electrical lines are disposed in a space between said first and second sections.

Embodiment 53: The endoscope of any of Embodiments 46-52, wherein said endoscope comprises an arthroscope.

Details of one or more implementations of the subject matter described in this disclosure are set forth in the accompanying drawings and the description below. Although the examples provided in this disclosure are primarily described in terms of a medical imaging device, the concepts provided herein may apply to other types of imaging systems and devices. Other features, aspects, and advantages will become apparent from the description, the drawings and the claims. Note that the relative dimensions of the following figures may not be drawn to scale.

DETAILED DESCRIPTION OF VARIOUS EMBODIMENTS

Some embodiments herein comprise endoscopes for viewing inside a cavity of a body. Various embodiments of the endoscopes comprise a plurality of lenses disposed within an elongate tubular structure having proximal and distal ends. These the lenses can relay an image of features in the body located at the distal end of the endoscope to the proximal end of the endoscope. In some embodiments, a detector such as a two-dimensional CCD or CMOS detector array can be included at the proximal end of the endoscope to sense the relayed image. In some embodiments, an eyepiece or other optics may be used to view the image. In certain embodiments, the endoscope may additionally have a light source that is configured, sized, and positioned so as to be inserted into the body cavity to provide illumination therein. In some embodiments, for example, this light source is disposed at the distal end of the endoscope. In various embodiments, this light source comprises at least one solid state emitter, such as a light emitting diode (LED), located at the distal end of the endoscope. One challenge of such a configuration is that the solid state emitters such as LEDs may generate heat as they emit light.

Accordingly, various embodiments disclosed herein are designed to conduct heat away from the LED at the distal end of the endoscope. One approach described herein is to employ a structure such as a cradle for holding the plurality of lenses that also is a conduit for extracting heat from the distal end of the endoscope where the LED is located. In some embodiments, for example, an endoscope may include a thermally conductive cradle or lens holder for holding the plurality of lenses that extends to the distal end of the endoscope. The thermally conductive cradle may comprise a highly thermally conductive material such as copper, aluminum, etc. The thermally conductive cradle may therefore be capable of conducting heat away from the distal end of the endoscope resulting in a lower temperature at the distal end of the endoscope or of the LED or other components at the distal end. In certain embodiments disclosed herein, the thermally conductive cradle may also be electrically conductive.

In operation, light emitted from the light source illuminate and is reflected off objects, surfaces, and features (e.g., walls) in the interior of the body cavity. A portion of the reflected light may be collected through an aperture at the distal end of the endoscope. This light may be directed along an optical path through the endoscope formed by the plurality of lenses disposed in the cradle so as to form an image of the objects, surfaces, features at the proximal end of the endoscope. In certain embodiments, the series of lenses can comprise rod lenses disposed inside the thermally conductive cradle. The light collected may then be directed to an optical sensor such as, for example, an optical detector array or an optical camera. Thus, an image of the object, surface, feature, etc. inside the body cavity can be viewed, for example, by the physician possibly on a display in communication with the detector.

Figure 1:
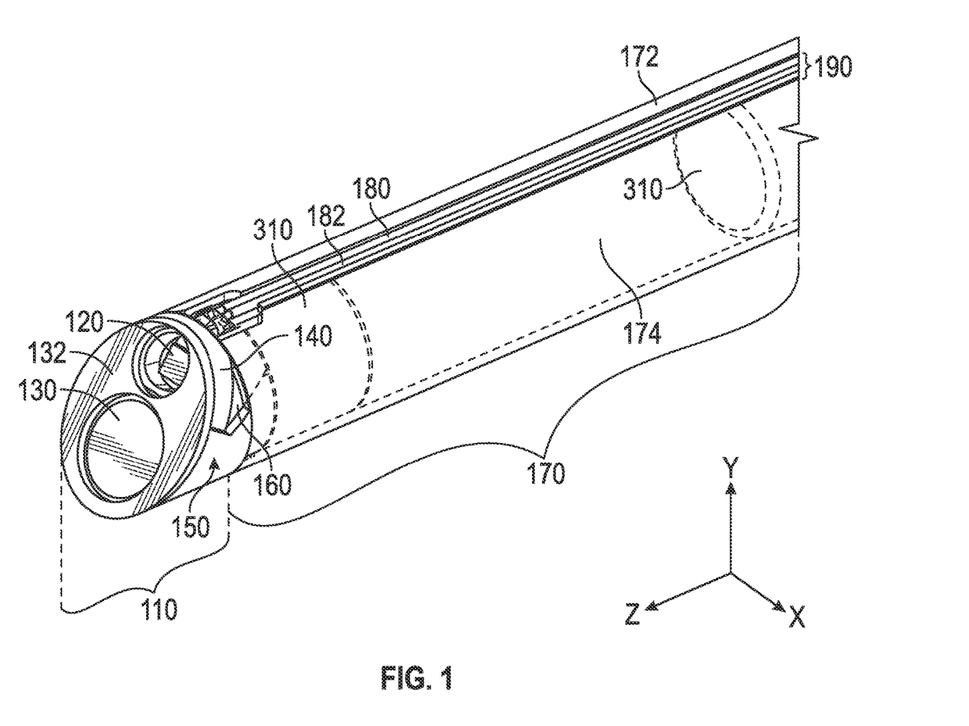
FIG. 1 illustrates a schematic perspective view of an endoscope, (e.g., an arthroscope), including a plurality of lenses supported within and by a lens cradle according to various embodiments disclosed herein.

For illustrative purposes, FIG. 1 illustrates a portion of an endoscope such as, for example, an arthroscope configured to conduct heat from the distal end thereof. The endoscope comprises an elongate member that may be inserted into a portion of a body such as a human body. Additional discussion of endoscopes is provided in U.S. patent application Ser. No. 11/099,435 (now U.S. Pat. No. 7,976,462) which is incorporated by reference herein in its entirety.

Referring to FIG. 1, the endoscope includes a distal end portion 110 and a lens cradle 170 attached to the distal end portion. The distal end portion 110 may include a solid state emitter 120. The solid state emitter 120 may be configured to radiate light and illuminate internal regions of the body. Although FIG. 1 illustrates one solid state emitter, in other embodiments a plurality of solid state emitters may be disposed at the distal end portion 110 of the endoscope, such as for example similar to the embodiments disclosed in U.S. patent application Ser. No. 11/099,435 (now U.S. Pat. No. 7,976,462) which is incorporated by reference herein in its entirety. In some embodiments, the solid state emitter 120 emits white light, although the emitter 120 does not need to be a white light emitter. A colored emitter that radiates in narrow wavelength ranges may be employed as well. For example, images may be formed by optical sensors that are sensitive to the particular wavelength region used for illumination. In certain embodiments, a specific wavelength illumination may be employed for fluorescence applications. Accordingly, the emitter may emit broad or narrow band ultraviolet as well as infrared light.

Figure 1A:
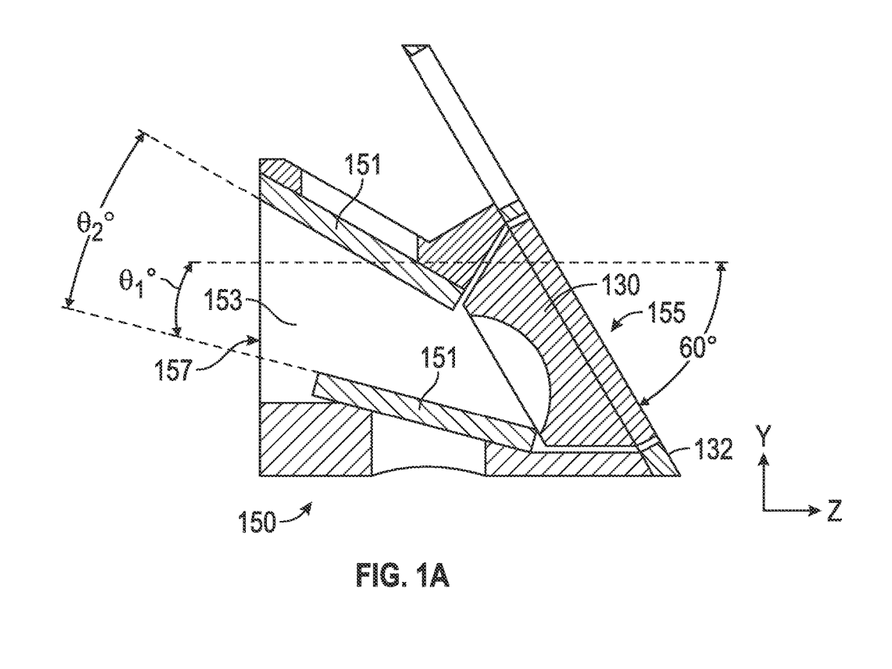
FIG. 1A & FIG. 1B illustrate schematic cross-sectional views of an "air prism" according to various embodiments disclosed herein.

Referring to FIG. 1, the distal end portion 110 may include an air prism block 150. FIG. 1A shows a cross-sectional view of such an air prism and air prism block 150. The air prism block 150 comprises a body having an input aperture 155, a passageway 153 through the body, and an output aperture 157. The body 150 includes internal sidewalls that define the passageway 153 through the body.

Reflectors 151 may be disposed in the passageway to assist the propagation of light therethrough. The embodiment shown includes two such reflectors 151. The reflectors 151 can be disposed at an angle $\theta_2$ with respect to each other as shown in FIG. 1A. The angle $\theta_2$ between the reflectors 151 can depend on the offset angle of the endoscope. For example, for a 30-degree offset endoscope, the angle $\theta_2$ can be about 15 degrees. As another example, for a 75-degree offset endoscope, the angle $\theta_2$ can be about 37.5 degrees. The reflectors 151 can also be angled with respect to a central axis of the endoscope. For example, as shown in FIG. 1A, one of the reflectors 151 is disposed at an angle $\theta_1$ with respect to the central axis of the endoscope. Without any loss of generality, in various embodiments, the angle $\theta_1$ can be equal to the angle $\theta_2$.

Figure 1B:
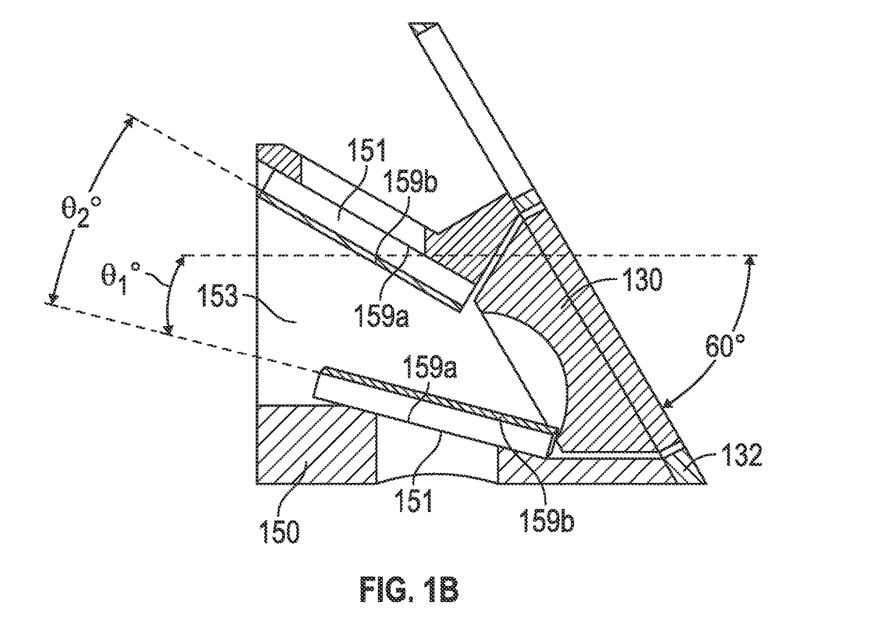

The reflectors 151 may comprise mirrors (as illustrated) and/or metallization for example on the sidewalls of the air prism block 150 that reflects light. In some embodiments, for example, mirrors comprising metalized glass plates are disposed on the internal sidewalls of the passageway 153. In such cases, light received through the input aperture 155 propagate through the passageway 153 being reflected off reflective surfaces of the reflectors 151 to the output aperture 157. FIG. 1B shows a cross-sectional view of an embodiment of an air prism including mirrors comprising a pair of metalized substrates. The substrates can comprise glass, ceramic, plastic, acrylic or any material that can provide sufficient structural support. The substrates have a first surface 159a adjacent the body 150 and a second surface 159b opposite the first surface 159a. The second surface 159b forms a portion of the boundary of the passageway 153. As illustrated in FIG. 1B, the second surface 159b of the substrate is metallized such that light collected at the distal end of the endoscope travels through the passageway by multiple reflections at the second surface 159b of the substrates towards the optical sensor. Metallizing the surface of the substrates adjacent the passageway can advantageously reduce or eliminate the amount of dispersion between the various wavelengths of light that can result when travelling through the material of the substrate. In some embodiments, the body 150 may comprise plastic, ceramic, or metal. In some embodiment the body 150 comprises thermal conducting material such as metal or thermally conducting ceramic. Various implementations of an endoscope including an air prism are also described in U.S. patent application Ser. No. 11/099,435 (now U.S. Pat. No. 7,976,462) which is incorporated by reference herein in its entirety.

Referring again to FIG. 1, the distal end portion 110 additionally comprises a front lens 130 and a cover plate 132. The front lens 130 is disposed in the input aperture 155 of the air prism block 150. The cover plate 132 is disposed over (or forward) the front lens 130 in front of the air prism block 150. The cover plate 132 includes a hole therein that is disposed with respect to the front lens 130 such that light can pass through the hole and to the front lens. Accordingly, the cover plate 132 is disposed on the air prism block 150 in a manner to align the hole in the cover plate with the front lens 130. Accordingly, light received by the front lens 130 can propagate into the input aperture 155 of the air prism 150 and therethrough. The cover plate 132 may comprise metal such as stainless steel in some embodiments, although other materials may be used.

The cover plate 132 also has a hole therein that is disposed with respect to the solid state emitter 120 to permit light to from the emitter to pass through the cover plate.

In various embodiments the front lens 130 comprises glass, sapphire, or other substantially optically transmissive or transparent material. In some embodiments, the front lens 130 has negative power. In certain embodiments, the front lens 130 comprises a plano-concave lens with a plano surface disposed outward (e.g., more distal). Accordingly, in various embodiments the front lens 130 collects light reflected from surfaces and/or features within the body cavity and this light propagates into the air prism, being reflected of the reflective surfaces therein, so as to exit the output aperture 157 of the air prism. The front lens 130 may provide for increased field of view and may be tilted at an angle with respect to the longitudinal direction (e.g., z-axis) so as to image sidewalls of the body cavity. Moreover, in some embodiments, the front surface of the distal end portion 110 may be angled so that light can be collected at the distal end of the endoscope from an oblique direction with respect to the endoscope. For example, the endoscope may be used to observe an inner side wall of a cavity in the body by inserting the endoscope into the cavity and rotating the endoscope such that the angled front surface is directed toward a portion of the inner side wall of the cavity. Other designs are possible.

Figure 3:
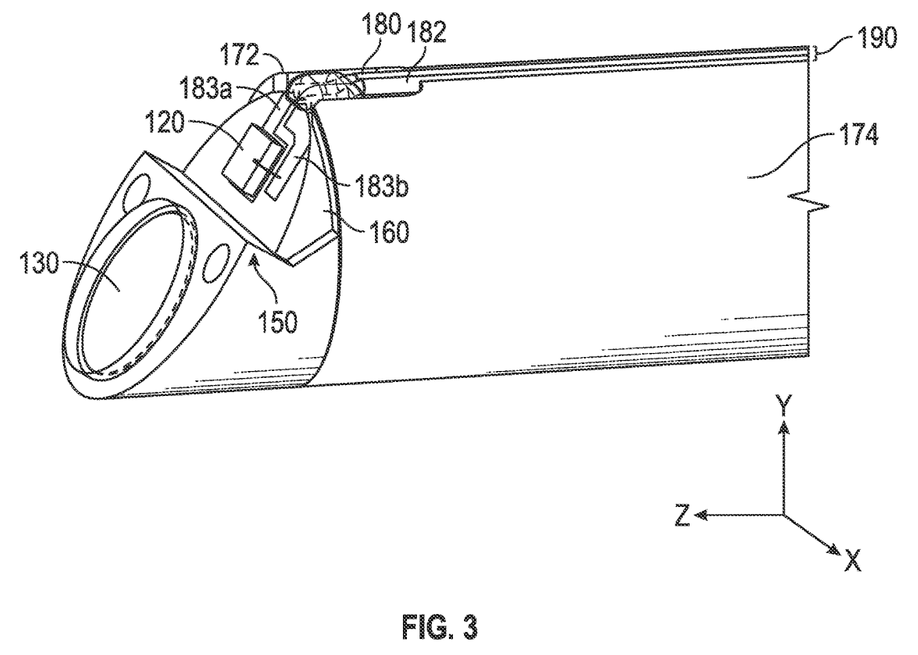
FIG. 3 illustrates a schematic view of the distal end portion of an endoscope showing the lens cradle as well as a solid state light emitter coupled to electrical lines disposed between two halves of the cradle.

The solid state emitter 120 may be mounted on a base 160. FIG. 3 shows an additional view of this base. In various embodiments the base 160 comprises thermal conducting material. In various embodiments, this base 160 comprises electrically insulating material. In certain embodiments, this base 160 comprises a thermal conducting insulator such as a ceramic. In various implementations, the base 160 can comprise materials, such as, for example, alumina (e.g. $Al_2O_3$) and/or nitride (e.g., silicon nitride). In addition, in certain embodiments, the base 160 may be coated with a coating to enhance the thermal conducting properties of the base 160. For example, the base 160 may be metalized such as with gold coating in order to provide the base 160 with thermally conductive and/or electrically conductive properties.

In various embodiments, the base 160 is configured to receive the emitter (e.g., LED) 120. For example, the base 160 may include holes for receiving pins disposed on the LED 120. These pins may comprise electrical connections to the emitter 120, for example, an anode and a cathode of a light emitting diode. The base 160 may be metallized and/or comprise metal pathways to provide electrical connections to the cathode and anode of the solid state emitter 120. These pathways may be formed from patterned metallization such as patterned gold. The base 160 is disposed in part on the air prism block 150. Further, as illustrated in FIG. 3, the base 160 may be in contact with the cradle 170 possibly over a large area. In various embodiments, this interface is a sufficient thermal contact to effectively transfers heat from the LED base 160 to the cradle 170. Accordingly, the base 160, being a strong thermal conductor, may assist in dissipating heat generated from the solid state emitter 120 away from the distal portion 110 of the endoscope for example, via the cradle 170 as discussed below.

As illustrated in FIG. 1, the distal end portion 110 further comprises a reflector 140. The reflector 140, in the embodiment shown, comprises a plate having an aperture therein. The aperture has a perimeter defined by a wall or surface. This surface may be at least partially reflecting and may be white or other reflecting color and/or may comprise reflective material such as a metal coating to reflect light. The plate 140 is disposed on the LED base 160 such that the LED 120 is within the aperture and framed by the reflecting surface. So configured, at least a portion of the light emitted in lateral and/or reward directions from the emitter may possibly be reflected forward. In various embodiments, the reflecting surface can have a shape or contour to enhance useful reflection. Accordingly, in various embodiments, the reflector 140 may be configured to reflect and redirect light so as to avoid wasting light. In some embodiments, the reflector plate 140 comprises thermal conducting material such as metal or thermally conducting ceramic. In various embodiments, the reflector plate 140 is in good thermal contact with the base 160.

As illustrated in FIGS. 1 and 3 and referenced above, the distal end portion 110 is connected to the lens cradle 170. In particular, in the embodiments below, the LED base 160 (and possibly the air prism block 150) are firmly attached to the distal end of the cradle 170 so as to provide a sufficiently good thermal contact to readily transfer heat from the LED base (and possibly the air prism block) to the cradle. As shown in FIG. 1, the lens cradle 170 provides an elongate support for one or more optical elements lenses 310. For example, the cradle 170 may surround, at least partially, rod lenses. Accordingly, the cradle 170 contains a central inner open region for housing the plurality of lenses 310. In various embodiments, this central inner open region is shaped such that the lenses 310, which may have cylindrical edges, fit conformally therein.

Accordingly, in various embodiments, the cradle 170 may comprise a hollow cylindrical tube or portions thereof. The hollow cylindrical tube may provide an optical path for propagating light from the distal end portion 110 of the endoscope to the proximal end of the endoscope. The cradle 170 may be a small, e.g., narrow, structure for non-invasive insertion into the body. In various embodiments, for example, the cradle 170 has a width of less than 5 mm or 4 mm but greater than 1 mm or 2 mm. In various embodiments the width or outer diameter is between about 3-4 mm. The walls of the cradle 170 may be thin to allow for lenses 310 having sufficient aperture size to be disposed in the central inner cavity region of the cradle, maintaining a small cross-section for the endoscope. In some embodiments, for example, the walls are less than 1 mm or 0.5 mm thick but may be larger than 0.1 mm thick in various embodiments. In some embodiments, the walls are between 0.2 and 0.3 mm thick. The cradle 170 may be substantially longer than wide. For example, the length of the cradle 170 (e.g. in the z direction) may be between 100 mm and 400 mm and between 200 mm and 300 mm and may be between 10, 20, 30, 40, 50 times or more the width thereof but less than 100, 90, 80, 70, or 60 times the width thereof in some embodiments.

Figure 2:
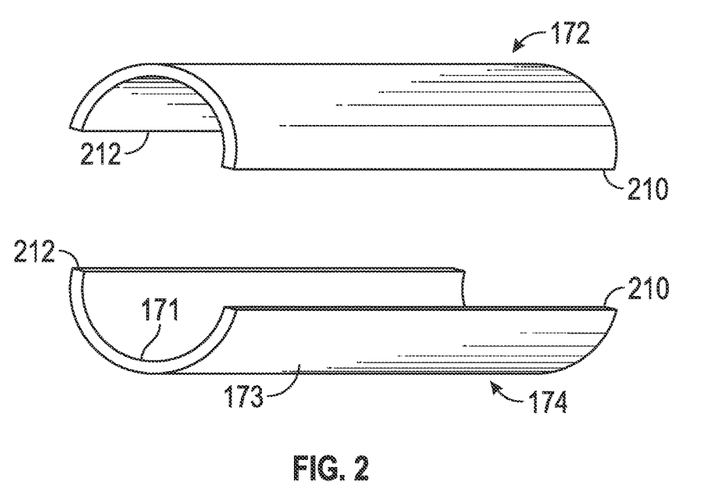
FIG. 2 illustrates a schematic exploded perspective view of an endoscope cradle comprising two portions or halves according to various embodiments disclosed herein.

Referring to FIGS. 1 and 2, in some embodiments, the cradle 170 comprises physically separate portions 172, 174 in the shape of a right circular cylinder split down its length, the longitudinal z-direction as shown. The separate components 172, 174, when assembled, may form or substantially form a right circular cylinder having the central open inner region for housing the lenses 310. In the embodiment shown in FIGS. 1 and 2, the cradle 170 is split into two physically separate components 172, 174, e.g., two halves 172, 174, in the shape of a right circular cylinder cut in half down its length. The separate portions (e.g., halves) 172, 174 may be substantially equal in size in some embodiments, although the sizes of the separate portions (e.g. two halves) may be different in others. Similar, the two components 172, 174 when put together, need not completely produce a right circular cylinder. As discussed below, for example, spaces may exist between the two halves 172, 174 when assembled to support the lenses 310 in the endoscope.

Referring to FIG. 2, each halve 172, 174, includes a concave inner surface 171 and a convex outer surface 173. The concave inner surface 171 is shaped to conformally fit the plurality of the lens 310 within the cradle 170 when the two halves 172, 174 are arranged together. Although the outer surface 173 is shown as convex, other shapes are possible. However, as discussed above, in various embodiments the cradle 170 is not very thick and thus a convex shaped outer surface 173 may likely accompany the concave inner surface 171.

Referring to FIG. 2, each half 172, 174 may include longitudinal edges 210, 212. The two halves 172, 174 may be arranged with respect to each other such that the longitudinal edges of the two halves are in proximity to each other. Referring to FIG. 1, the two halves 172, 174 may be separated by a space 190 disposed between the longitudinal edges 210, 212. In the embodiments shown, each of the two halves 172, 174 includes two longitudinal edges 210, 212. When the two halves 172, 174 are disposed together to form the assembled cradle 170, each of the longitudinal edges 210, 212 of one half 172, 174 may be separated from the longitudinal edges of the other half 172, 174 by the pair of spaces 190. In some embodiments discussed more fully below, the two halves 172, 174 may be physically separated so as to electrically isolate the two halves 172, 174. However, in some embodiments one or both of the spaces 190 are not present and the two halves 172, 174 touch each other instead of having a space therebetween. In certain embodiments, for example, one space is included between longitudinal edges 210 of respective halves whereas the other longitudinal edges 212 of the respective edges touch each other. In various embodiments, the space 190 (whether one or two) is greater than 0.1, 0.2, 0.3, 0.4, 0.5, 0.6, 0.8, 0.9, and 1.0 millimeters and smaller than 5 mm, 4 mm, 3 mm, 2 mm, 1 mm, 0.8 mm, or 0.6 mm. For example, in some embodiments at least one of the spaces is greater than 0.4 mm and less than 0.6 mm. In some embodiments, at least one of the spaces is greater than 0.9 mm and less than 2.0 mm. Other ranges are possible.

In various embodiments, the inner surface 171 of the cradle 170 is smooth and does not include surface features on the inner surface to space the lenses 310 from each other. Such a design, simplifies the manufacture of the cradle 170. For example, the cradle 170 or the separate halves 172, 174 of the cradle can be extruded in some embodiments. To space the lenses 310 apart, the lenses are appropriately placed with the proper longitudinal spacing therebetween in the cradle 170 or the cradle portions 172, 174 are disposed about the appropriately space lenses. Robotics may be employed to place the lenses 310 with the appropriate spacing between the lenses. In other, other embodiments, however, surface features may be include on the inner surface 171 of the cradle 170 or spacers may be included between the lenses 310.

As discussed above, in various embodiments, the solid state emitter 120 may generate substantial heat. Accordingly, referring to FIG. 1, in some embodiments the cradle 170 may substantially entirely comprise a thermally conductive material, such as copper or aluminum. In certain embodiments, for example, the cradle 170 comprises at least 90%, 95% or more and up to 99% or 100% copper. Similarly, in certain embodiments, the cradle comprises at least 90%, 95% or more and up to 99% or 100% aluminum. In certain embodiments, the cradle 170 comprises at least 90%, 95% or more and up to 99% or 100% other highly conductive material such as a copper alloy or other metal. Forming the cradle 170 of highly thermally conductive material can enable heat generated by the solid state emitter 120 to be dissipated away from the distal end portion 110 of the endoscope where the emitter 120 is disposed. By transferring heat away from the distal end portion 110 of the endoscope, the thermally conductive cradle 170 advantageously allows the use of bright solid state emitters 120 that may generate significant heat without excessive heating at the distal end of the endoscope. Accordingly, for some embodiment, during use, the thermally conductive cradle 170 may allow the endoscope to remain within five degrees of body temperature.

In various embodiments, the plurality of lenses 310 comprises rod lenses. The rod lenses may be disposed in the inner central open region of the cradle, for example, formed when the two halves 172, 174 are assembled with respect to each other. Accordingly, the rod lenses may be disposed in an optical path from the distal portion 110 of the endoscope to the proximal portion of the endoscope at least in part within the inner region of the cradle 170. The optical path may provide a path through which collected light travels. In particular, the light from the emitter 120, some of which is reflected from the reflector 140, may be reflected or scattered from the portion of a body cavity illuminated by the solid state emitter 120. The lens 130 may be configured to collect this light. The air prism 150 may be configured to redirect light entering the lens 130, such that light will propagate through the cradle 170 parallel to the longitudinal axis (e.g., z-axis) of the cradle 170 and to, for example, the 2D optical detector or an eyepiece, etc.

As illustrated in FIGS. 1 and 3, in various embodiments the endoscope may include two electrical lines 180, 182 which extend along the longitudinal length of the cradle 170. The two electrical lines 180, 182 may electrically connect to the solid state emitter 120, e.g., the cathode and anode of an LED. In particular, the two electrical lines 180, 182 may be connected to metallization 183*a*, 183*b* (see FIG. 3) on the LED base 160 that is configured to electrically connect to conducting pins or electrical leads on the emitter 120. The two electrical lines 180, 182 may comprise electrical wires such as copper or aluminum wires having insulation thereon. Other types of wiring such as cables may be used.

Referring to FIGS. 1 and 3, the space 190 may provide room for the two electrical lines 180, 182 which connect to the cathode and anode of the solid state emitter 120. Other designs, however, are possible.

In some embodiments, the endoscope does not include or use these two lines 180, 182, extending along the longitudinal length of the copper tube 170. Instead in these embodiments, each half 172, 174 of the cradle 170 may be employed as an electrical conductor or line for transmitting electrical power. For example, each half 172, 174 may be electrically connected to the emitter 120, for example, to the respective cathode and anode of the LED. Thus, each half 172, 174, of the cradle 170 may itself comprise the anode or cathode. In some embodiments, the two halves 172, 174 are electrically connected to metallization 183*a*, 183*b* on the LED base 160 to form the electrical connection to the emitter 120. In various embodiments, the two halves 172, 174 may be electrically isolated by spaces 190 between the longitudinal edges 210, 212 of the two halves 172, 174. Electrically insulating spacers may also be employed. Although use of the cradle 170 as one or more conductive lines is discussed above as an alternative to using wires 180, 182, in some embodiments, both electrical wires 180, 182 as well as the conducting cradle 170 can be used to transfer electrical signals and/or power between the distal and proximal portions of the endoscope.

In various of these embodiments, the cradle 170 comprises an electrically conductive material, such as copper, thus allowing the cradle 170 to carry electricity. The cradle 170 may thereby operate as an electrical path for providing power or grounding to the solid state emitter 120. In these embodiments, electrical isolation of the cradle 170 and/or halves 172, 174 thereof may be useful to prevent shorts, for example, with an outer tube that fits over the cradle as this outer tube may comprise stainless steel and be conductive. One or more insulating coating may be disposed on the cradle 170, e.g., the outer surface of the cradle, or on the outer tube, e.g., an inner surface of the outer tube, or both. In implementations where the cradle 170 is configured to be electrically conducting and used to carry electricity, an insulating material can be disposed between the distal end 110 and the cradle 170. For example, an insulating material can be disposed between the cover 132 and the cradle 170.

Figure 4:
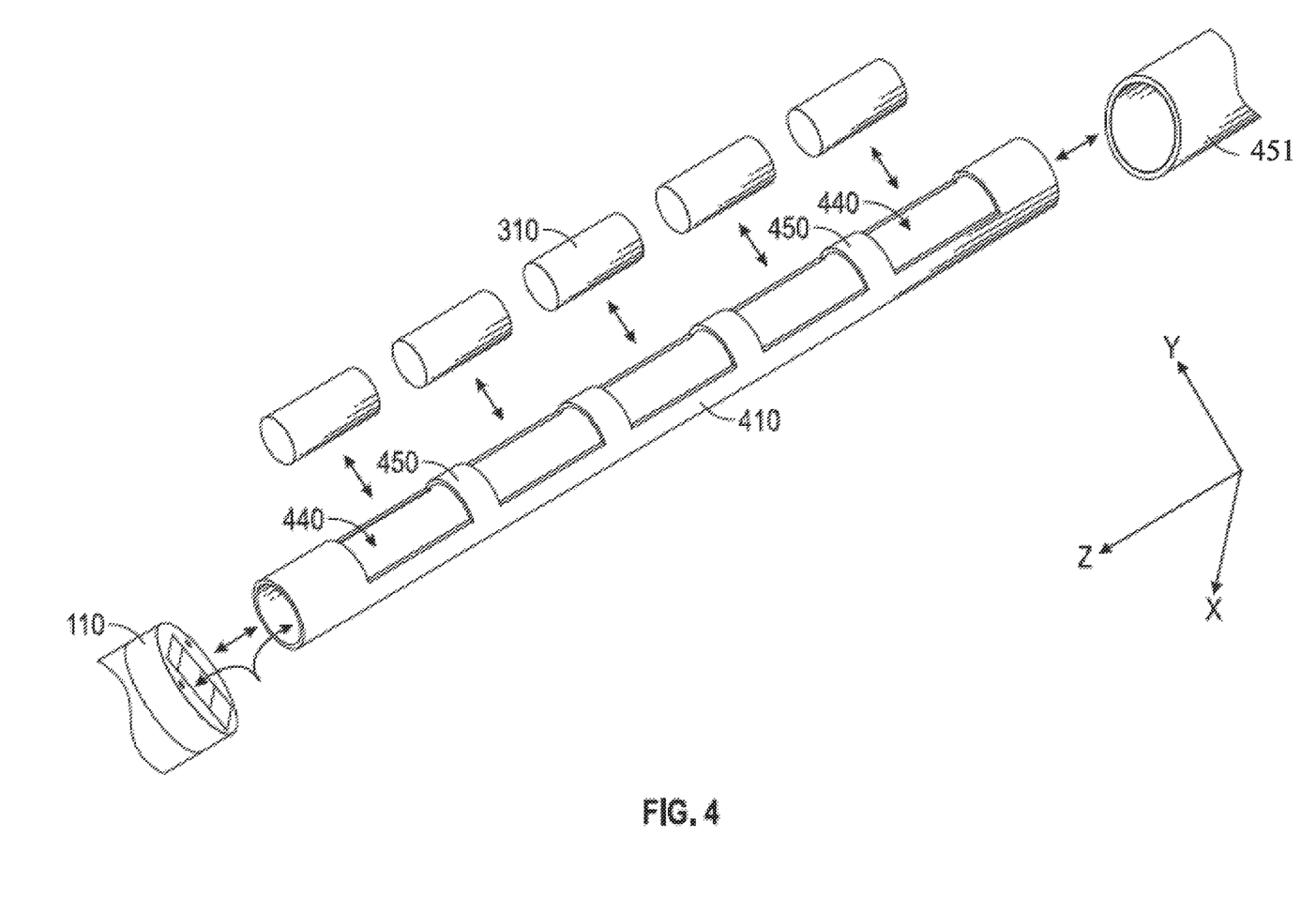
FIG. 4 illustrates a schematic exploded perspective view of a unitary cradle for supporting a plurality of rod lenses and an outer tube configured to surround the cradle and lenses.

FIG. 4 illustrates some embodiments wherein the endoscope comprises an inner cradle 410 and an outer tube 451. Various aspects of the implementation illustrated in FIG. 4 can be similar to the implementations of endoscopes disclose in U.S. patent application Ser. No. 11/099,435 (now U.S. Pat. No. 7,976,462) which is incorporated by reference herein in its entirety. As discussed above, the inner cradle 410 may comprise a thermally conductive material, such as copper, aluminum, etc. in order to dissipate heat generated by the solid state emitter 120 away from the distal portion 110 of the endoscope. In addition, the outer tube 451 may comprise a thermally conductive material, such as aluminum, stainless steel, or the like. Thus, the outer tube 451 may also conduct heat generated by the solid state emitter 120 away from the distal portion 110 of the endoscope.

In various embodiments, the inner cradle 410 may comprise an electrically conductive material, such as copper, to carry electricity. Accordingly, as discussed above, in some embodiments, the endoscope includes an insulator between the inner cradle 410 and the outer tube 451, in order to prevent shorting out the outer tube 451. In some cases, the inner cradle 410 may include an insulating coating on the exterior of the inner cradle 410. Alternatively, the outer tube 451 may include an insulating coating on the interior of the outer tube 451. In some embodiments, both may be employed. Also insulating spacers between the inner cradle and outer tube may be employed.

As discussed above, with continued reference to FIG. 4, the inner cradle 410 may function as a support structure for one or more lenses 310. In the embodiment shown in FIG. 4, however, the inner cradle 410 has a plurality of slots 440 (five shown) each configured to hold a rod lens 310. The slots 440 may be separated by space portions 450 (four shown) that are each sized and positioned so as to provide proper alignment and longitudinal separation of the rod lenses 310 for suitable relay of an image therethrough. In other words, the spacing between the slots 440 may be defined by spacer portions 450 so as to longitudinally space the rod lenses 310 with respect to each other according to the optical design prescription. In some embodiments, the spacers 450 between the slots provide for structural support and stability to the cradle 410, which comprises thin walls and is susceptible to bending.

In various of these embodiments, during operation, at least the distal portion 110 of the endoscope is inserted into a body cavity. An electrical power signal is provided to the solid state emitter 120, causing the solid state emitter to emit light and generate heat. The thermally conductive cradle 170 dissipates heat away from the distal portion 110 of the endoscope. The thermally conductive cradle 170 may also be electrically conductive, such that the cradle 170 provides an electrical path for providing power or grounding to the solid state emitter 120. Light emitted by the solid state emitter 120 is reflected off an object within the body cavity. A portion of the reflected light is collected by a lens 130. The light is then directed through a plurality of lens elements, such as rod lenses 310, disposed in the cradle 170. Thus, the light propagates from the distal portion 110 of the endoscope to the proximal portion of the endoscope.

Other variations, however, are possible. In certain embodiments, the electrical lines 180, 182 that extend from the proximal end of the endoscope to the emitter 120 have sufficient size coupled with the thermal conductivity thereof, to operate as conduits of thermal energy so as to sufficiently dissipate heat from the emitters and/or distal end of the endoscope. The electrical lines may, for example, comprise cable such as a ribbon cable having sufficient mass and cross-sectional area (in the transverse direction such as x- and/or y-directions) to transfer enough heat away from the emitter to maintain the distal portion of the endoscope at suitable temperatures for insertion into the body. In such embodiments, the electrically conducting cradle 170, 410 within the outer tube 451 may be excluded. The hollow outer tube 451, instead, may have a size such the lenses 310 are held in place within an inner region of the hollow outer tube without the cradle 170, 410.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Additionally, other embodiments are within the scope of the following claims. In some cases, the actions recited in the claims can be performed in a different order and still achieve desirable results.

What is claimed is:

1. An endoscope, comprising:
a proximal end portion;
a distal end portion;
a plurality of lenses disposed in an optical path extending from said distal end portion to said proximal end portion such that an image of an object at the distal end portion can be formed at the proximal end portion;
at least one solid state emitter disposed at the distal end portion, the at least one solid state emitter generating heat when activated; and
a thermally conductive elongate assembly forming an elongate inner open region configured to house said plurality of lenses, said thermally conductive elongate assembly attached to the distal end portion, the thermally conductive elongate assembly configured to dissipate heat generated by the at least one solid state emitter away from the distal end portion,
wherein the thermally conductive elongate assembly comprises separate first and second curved sections, wherein the first curved section comprises a first half of a right circular cylinder and the second curved section comprises a second half of the right circular cylinder, wherein each of the first curved section and the second curved section is electrically conductive and comprises copper,
wherein the first curved section is electrically connected to a first electrode of said at least one solid state emitter and the second curved section is electrically connected to a second electrode of said at least one solid state emitter, and
wherein the first curved section and the second curved section are electrically isolated from each other by an electrically insulating material, an air gap, or both.

2. The endoscope of claim 1, wherein said endoscope is an arthroscope.

3. The endoscope of claim 1, wherein the at least one solid state emitter comprises at least one light emitting diode.

4. The endoscope of claim 1, wherein said plurality of lenses comprise rod lenses having lengths and widths, said lengths being longer than said widths.

5. The endoscope of claim 1, wherein the first and second curved sections have substantially equal size.

6. The endoscope of claim 1, wherein the first curved section and the second curved section each has two longitudinal edges, and wherein a first longitudinal edge of the first curved section and a first longitudinal edge of the second curved section are separated by a space at least 0.5 millimeter.

7. The endoscope of claim 6, wherein a second longitudinal edge of the first curved section and a second longitudinal edge of the second curved section are physically separated by a space.

8. The endoscope of claim 6, wherein a second longitudinal edge of the first curved section and a second longitudinal edge of the second curved section are physically spaced apart by a spacer.

9. The endoscope of claim 1, further comprising an outer tube surrounding the thermally conductive elongate assembly.

10. The endoscope of claim 9, wherein said thermally conductive elongate assembly is electrically insulated from said outer tube.

11. The endoscope of claim 1, wherein the distal end comprises a passageway forming a portion of the optical path, wherein the passageway comprises first and second reflective surfaces, such that the portion of the optical path through the passageway does not include a glass optical element.

12. The endoscope of claim 1, wherein the first curved section and the second curved section are electrically isolated from each other by an electrically insulating material.

13. The endoscope of claim 1, wherein the first curved section and the second curved section are electrically isolated from each other by an air gap.

14. An endoscope, comprising:
a proximal end portion;
a distal end portion;
at least one solid state emitter disposed at the distal end portion, the at least one solid state emitter generating heat when activated;
an elongate assembly attached to the distal end portion, wherein the elongate assembly is thermally conductive and configured to dissipate heat generated by the at least one solid state emitter away from the distal end portion, wherein the elongate assembly is further electrically conductive and is configured to provide an electrical path to the at least one solid state emitter; and
at least one lens disposed inside the elongate assembly,
wherein the elongate assembly comprises separate first and second curved sections, wherein the first curved section comprises a first half of a right circular cylinder and the second curved section comprises a second half of the right circular cylinder, wherein each of the first curved section and the second curved section is electrically conductive and comprises copper,
wherein the first curved section is electrically connected to a cathode of said at least one solid state emitter and the second curved section is electrically connected to an anode of said at least one solid state emitter, and
wherein the first curved section and the second curved section are electrically isolated from each other by an electrically insulating material, an air gap, or both.

15. The endoscope of claim 14, wherein the first curved section and the second curved section are electrically isolated from each other by an electrically insulating material.

16. The endoscope of claim 14, wherein the first curved section and the second curved section are electrically isolated from each other by an air gap.

17. An endoscope, comprising:
a proximal end portion;
a distal end portion;
a plurality of lenses disposed in an optical path extending from said distal end portion to said proximal end portion such that an image of an object at the distal end portion can be formed at the proximal end portion;
at least one solid state emitter disposed at the distal end portion, the at least one solid state emitter generating heat when activated; and
a thermally conductive elongate assembly comprising an elongate inner open region configured to house said plurality of lenses, said thermally conductive elongate assembly attached to the distal end portion,
wherein the thermally conductive elongate assembly comprises separate first and second curved sections, wherein each of the first curved section and the second curved section comprises substantially a half of a right circular cylinder, wherein each of the first curved section and the second curved section is electrically conductive and comprises copper,
wherein the first curved section is electrically connected to a cathode of said at least one solid state emitter and the second curved section is electrically connected to an anode of said at least one solid state emitter, and
wherein the first curved section and the second curved section are electrically isolated from each other by an electrically insulating material, an air gap, or both.

18. The endoscope of claim 17, wherein the first curved section and the second curved section are electrically isolated from each other by an electrically insulating material.

19. The endoscope of claim 17, wherein the first curved section and the second curved section are electrically isolated from each other by an air gap.

20. The endoscope of claim 17, wherein said endoscope is an arthroscope.

21. The endoscope of claim 17, wherein the at least one solid state emitter comprises at least one light emitting diode.

22. The endoscope of claim 17, wherein said plurality of lenses comprise rod lenses having lengths and widths, said lengths being longer than said widths.

23. The endoscope of claim 17, wherein the first and second curved sections have substantially equal size.

24. The endoscope of claim 17, wherein the first curved section and the second curved section each has two longitudinal edges, and wherein a first longitudinal edge of the first curved section and a first longitudinal edge of the second curved section are separated by a space at least 0.5 millimeter.

25. The endoscope of claim 24, wherein a second longitudinal edge of the first curved section and a second longitudinal edge of the second curved section are physically separated by a space.

26. The endoscope of claim 24, wherein a second longitudinal edge of the first curved section and a second longitudinal edge of the second curved section are physically spaced apart by a spacer.

27. The endoscope of claim 17, further comprising an outer tube surrounding the thermally conductive elongate assembly.

28. The endoscope of claim 27, wherein said thermally conductive elongate assembly is electrically insulated from said outer tube.

29. The endoscope of claim 17, wherein the distal end comprises a passageway forming a portion of the optical path, wherein the passageway comprises first and second reflective surfaces, such that the portion of the optical path through the passageway does not include a glass optical element.

* * * * *